(12) United States Patent
Gabele et al.

(10) Patent No.: US 6,371,326 B1
(45) Date of Patent: Apr. 16, 2002

(54) STERILE CONTAINER FOR MEDICAL PURPOSES

(75) Inventors: Lorenz Gabele, Sauldorf; Wolfgang Schwanke, Rietheim-Weilheim, both of (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

(21) Appl. No.: 09/592,081

(22) Filed: Jun. 12, 2000

Related U.S. Application Data

(63) Continuation of application No. PCT/EP98/08068, filed on Dec. 10, 1998.

(30) Foreign Application Priority Data

Dec. 13, 1997 (DE) .......................................... 197 55 532

(51) Int. Cl.[7] .............................................. B65D 55/02
(52) U.S. Cl. ........................ 220/326; 292/71; 206/373
(58) Field of Search ................................ 220/324, 326; 292/71, 76, 121, 109, 129, 69, 80, 113; 206/366, 373

(56) References Cited

U.S. PATENT DOCUMENTS

| | | | | |
|---|---|---|---|---|
| 233,195 A | * | 10/1880 | Bradley | ....................... 220/326 |
| 1,089,066 A | * | 3/1914 | Meyer | ....................... 220/326 |
| 1,382,499 A | * | 6/1921 | Gifford | ....................... 220/326 |
| 1,483,953 A | * | 2/1924 | Rainey | ....................... 220/326 |
| 4,331,257 A | | 5/1982 | Taschner | |
| 4,349,118 A | * | 9/1982 | Sanderson et al. | |
| 4,562,047 A | * | 12/1985 | Sestak et al. | |
| 4,818,502 A | | 4/1989 | Taschner | |
| 5,310,049 A | * | 5/1994 | Takimoto | ................ 220/326 X |
| 5,452,926 A | * | 9/1995 | Takimoto | ..................... 292/113 |
| 5,655,799 A | * | 8/1997 | Takimoto | ..................... 292/113 |

FOREIGN PATENT DOCUMENTS

| | | |
|---|---|---|
| DE | 82 13 349 | 5/1982 |
| DE | 35 42 404 | 6/1987 |
| DE | 41 27 893 | 2/1993 |
| GB | 01818 | 4/1909 |
| GB | 1171420 | 11/1969 |

* cited by examiner

Primary Examiner—Nathan J. Newhouse
(74) Attorney, Agent, or Firm—Barry R. Lipsitz; Douglas M. McAllister

(57) ABSTRACT

In order, in the case of a sterile container for medical purposes having a tub-shaped lower portion and a lid positionable thereon in sealing manner, which lid may be clamped against the lower portion by a closure, wherein the closure comprises a flap swivellable between an open position and a closed position, said flap having a locking projection, and a locking lug with a recess for accommodating the locking projection when the flap is in the closed position, to be able better to accommodate structural tolerances, it is proposed that the locking projection be mounted in the flap so as to resiliently displaceable in a direction in which it is moved out of the recess in the locking lug.

16 Claims, 3 Drawing Sheets

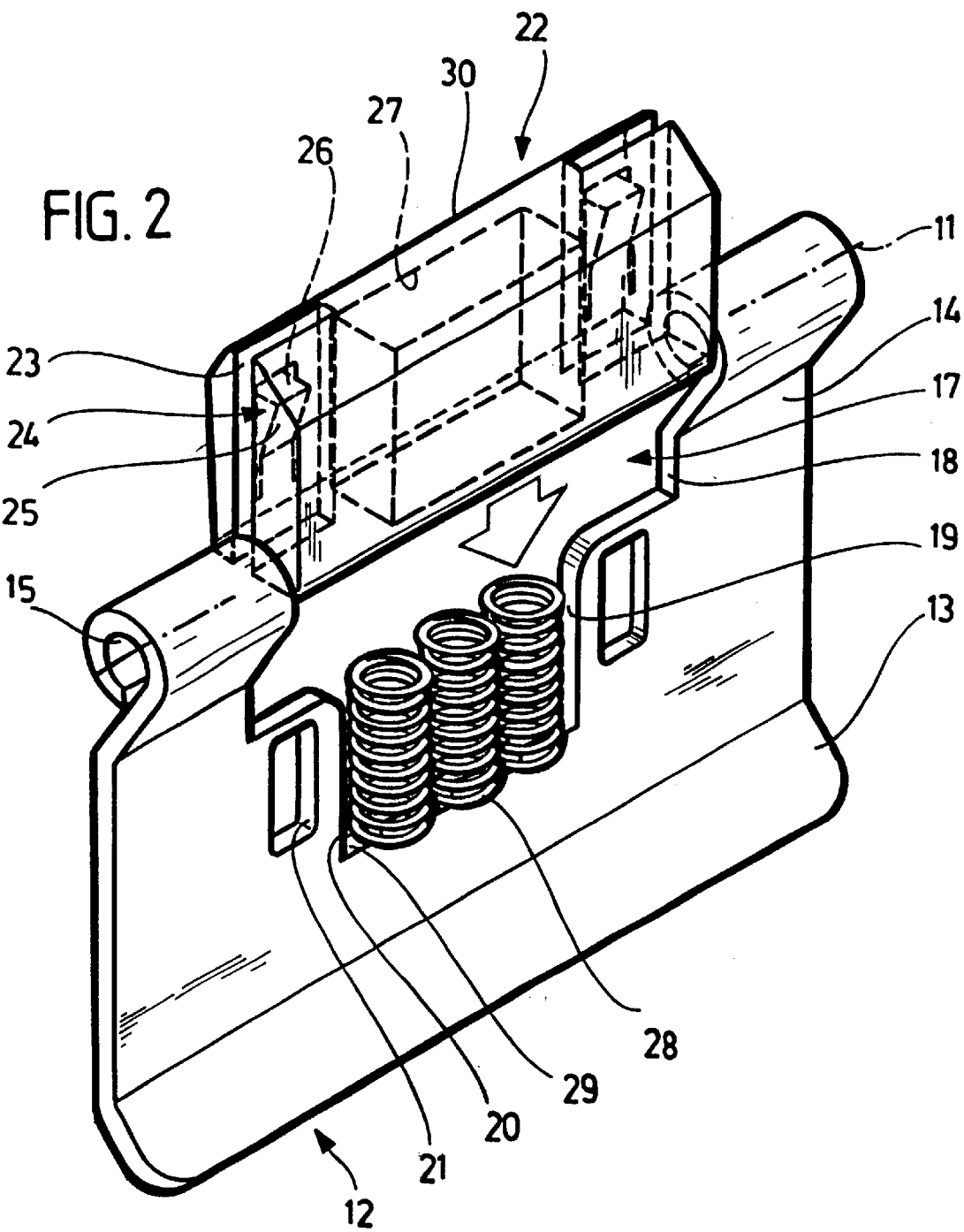

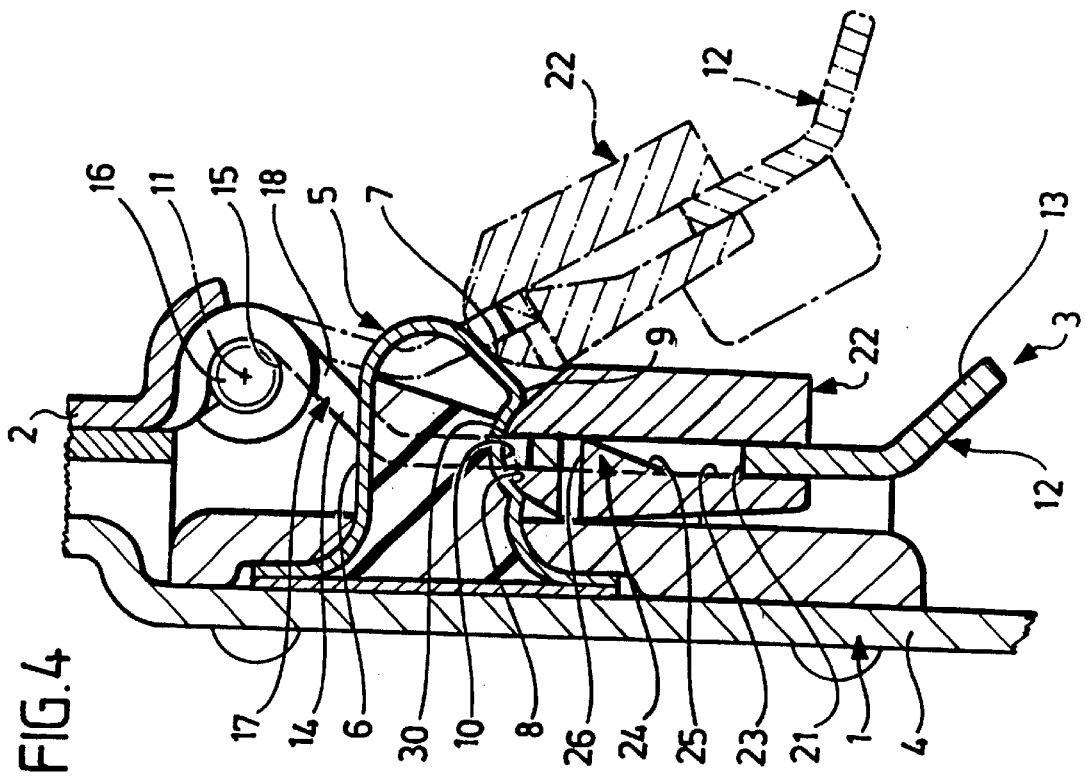
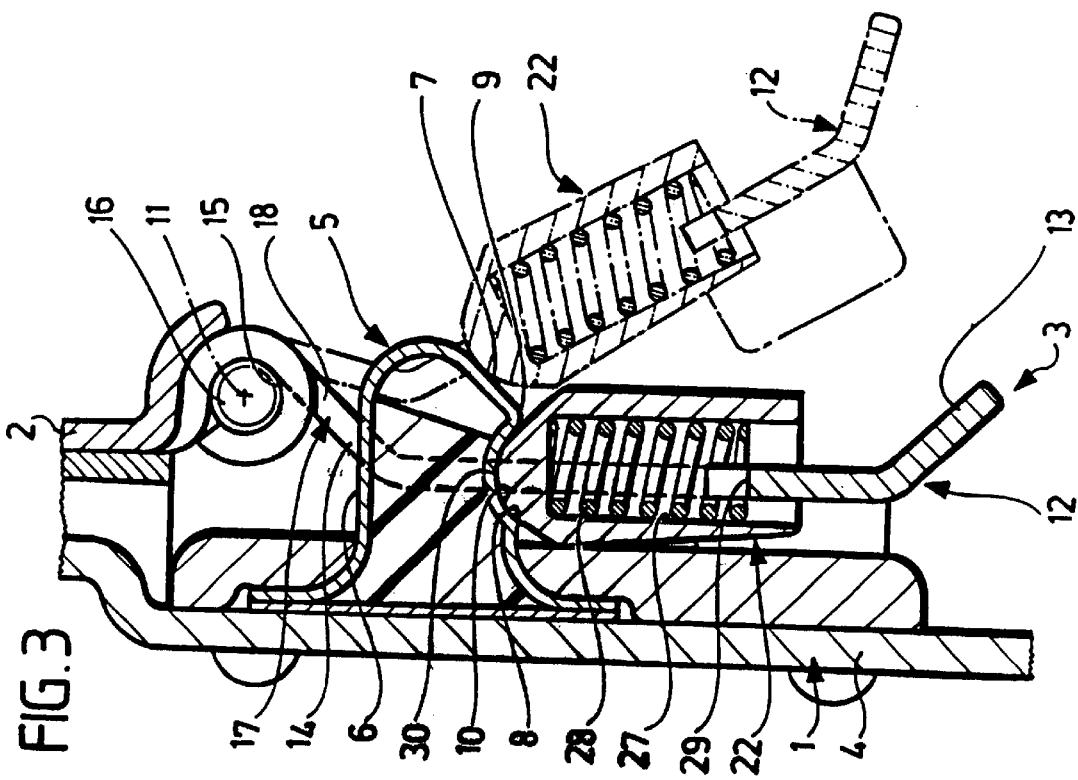

STERILE CONTAINER FOR MEDICAL PURPOSES

This application is a continuation of International application No. PCT/EP98/08068, filed Dec. 10, 1998.

BACKGROUND OF THE INVENTION

The invention relates to a sterile container for medical purposes having a tub-shaped lower portion and a lid positionable thereon in sealing manner, which lid may be clamped against the lower portion by a lock, wherein the lock comprises a flap swivellable between an open position and a closed position, said flap having a locking projection, and a locking lug with a recess for accommodating the locking projection when the flap is in the closed position.

Such sterile containers are closed in sealed manner in that a resiliently deformable seal is arranged between lid and tub. If the lid is clamped against the tub, this seal is resiliently compressed and ensures that a reliable seal is established around the entire circumference. Clamping together is enable by a special closure, which, in the case of known sterile containers, comprises a flap mounted swivellably on one portion (lid or lower portion) and a locking lug fixed to the other portion. The entire locking lug is capable of resilient deformation, such that a locking projection on the flap engage in a locking recess in the locking lug when said flap swivels, the locking lug undergoing such resilient deformation upon said swivelling movement that the locking projection may slide into the locking recess. The clamping force required for clamping lid and lower portion together is supplied by the resilience of the locking lug.

Although this design has proven very convenient and is therefore also used very widely, certain difficulties do arise in compensating manufacturing tolerances and in establishing the necessary clamping force between lid and lower portion.

SUMMARY OF THE INVENTION

The object of the invention is to so develop a sterile container of the generic type that the design thereof allows better compensation of manufacturing tolerances and optionally also better adjustment of the clamping force between lid and lower portion.

This object is achieved according to the invention for a sterile container of the above-described type in that the locking projection in the flap may be displaced resiliently in a direction in which it is moved out of the recess in the locking lug.

With the new design, therefore, the locking projection in the flap is in turn of resiliently displaceable construction and, in accordance with the dimensions of the flap, a relatively large displacement path is available thereto which is as a rule substantially larger than the displacement path provided by a resiliently deformable locking lug. This extension of the displacement path eases adaptation to manufacturing tolerances and it is additionally possible to vary the spring fore with which the locking projection is displaced in the direction of the recess.

In principle, it is possible to make the locking projection in one piece with the flap, resilient deformability then being achieved in the resiliently deformable connecting members are arranged in the connecting area between locking projection and flap, for example spring-type webs or the like.

In a particularly preferred embodiment, however, provision is made for the locking projection to take the form of a locking member separate from the flap, which locking member is mounted in the flap so as to be displaceable in a guide. Such a construction has the advantage that it is particularly simple to produce and, in addition, different materials may be used, for example the locking projection may consist of a sterilisable plastics material while the flap consists of metal.

It is beneficial for the guide to be open at one end and closed at the other end. This makes it particularly easy to insert the locking member, which is simply introduced into the guide from the open side. This open end may preferably face the swivel axis of the flap.

A particularly easily produced guide takes the form of the edge strips of a cutout portion of the flap, which strips engage in lateral longitudinal channels in the locking member.

It is also advantageous for the locking member to be held captive in the guide by a limit stop which may be moved resiliently out of engagement when the locking member is introduced into the guide. In particular, such a limit stop may take the form of a resilient catch, which engages in a recess extending in parallel with the guide.

In this way, assembly is made particularly simple, it being sufficient to introduce the locking member into the guide from the open side, the limit stop being brought resiliently out of engagement until the locking member is introduced into the guide. Then the limit stop moves back into the rest position and from this moment prevents withdrawal of the locking member from the guide.

Spring means are preferably arranged between the locking member and the flap, which effect the resilient displacement of the locking member.

These may be conventional spring means, for example helical springs.

It is beneficial for the flap and/or the locking member to comprise a receiving space for the spring means, such that the latter are inserted only loosely between flap and locking member and are then held in the receiving space, additional retaining means then being superfluous.

In a particularly preferred embodiment, provision is made for the receiving space to be so dimensioned that it may accommodate as spring means several compression springs next to one another. This allows the resilient forces with which the locking member is displaced in the direction of the recess in the locking lug to be varied by the insertion of different numbers of such compression springs. In this way, the clamping forces exerted by such a closure may be adjusted, which is of great significance, since the clamping forces required for obtaining uniform deformation of the seal between lid and lower portion increase in proportion to the length of the seal, such that different clamping forces are required for different sizes of container. These forces may be easily adjusted by the number of compression springs selected and in this way the same closure design may be used for containers of different sizes. Through an appropriate choice of spring force, it is also possible to adapt the clamping force to special sealing characteristics of the seal, the clamping force of the compression springs being less for soft seals than for hard seals.

It is particularly advantageous if the spring means are pretensioned in the relaxed end position. Through appropriate selection of the spring characteristics of the compression springs, this allows a resilient restoring force to be generated which is substantially without variation over the entire displacement distance of the locking member, such that these restoring forces remain extensively the same even where dimensions vary for structural reasons.

A particularly space-saving and favourable design is obtained if the locking member is mounted so as to be displaceable in the plane of the flap in the direction of the swivel axis thereof.

The flap may be in particular of U-shaped construction, with two limbs which define the swivel axis at their free ends and with a central cutout which accommodates the locking member.

In principle, given the above-described design of the flap with a resiliently displaceable locking projection, it is not necessary for the locking lug in turn to be of resilient construction; however, a preferred embodiment provides for the locking lug to be of resilient construction in such a way that, when the flap swivels, it moves slightly to make way for the locking projection on the flap. This is particularly useful where it is desirable for the locking member to effect as slight as possible a displacement movement, for example for dimensional reasons, such that then both the locking lug and the locking projection assume responsibility for part of the resilient displacement of the closure parts.

The resilience of the closure parts may provide such a long-stroke construction that, even when the closure is in place, the lid may be moved far enough away from the tub-shaped lower portion against the resilient closing force of the closure that an opening is formed between lid and tub-shaped lower portion. This embodiment has the advantage that the lid may thereby be raised resiliently from the tub such that any excess pressure prevailing inside the latter may be released. Thus, if the resilient closing forces are selected appropriately, the removal of air from the container may be performed during the sterilisation process, for example, without its being necessary to provide the container with a separate outlet valve or a separate outlet opening for the air. In addition, in the after-drying stage, which takes the form of a vacuum stage in conventional steam sterilisers, lifting of the lid may serve to dry the container contents. The moisture-saturated atmosphere is extracted from inside the container through the opening produced between tub and lid.

Such a sterile container construction is particularly advantageous in the case of a closure construction as described here, i.e. in the case of a closure having a swivellable flap with locking projection and locking lug. In principle, however, such a construction may be used for all sterile containers in which the lid is pressed resiliently against the tub by a closure, irrespective of the particular construction of the closure. The only essential factor is that the closing force is applied resiliently over a relatively long displacement path, such that the stroke which the lid may effect against the resilience is long enough for the lid to be capable of being lifted from the tub. The stroke has optionally to be long enough to take account of the deformation of a resilient seal between lid and tub.

It is beneficial for the sterile container to be closed completely when the lid is positioned sealingly thereon and for the inside thereof to be connected with the surroundings only by means of an inlet valve, which may be spring-loaded. An outlet valve is no longer necessary in the event of such a design, however, since the function of the outlet valve is assumed by the resiliently raisable lid.

It may further provided that a lifting element is arranged on the lid, by means of which the lid may be moved away from the tub against the action of the resilient closing force of the closure when the latter is in place. This is significant when, for example during the drying stage, it is intended that lifting of the lid should be effected not only as a result of the excess pressure inside the container but also deliberately from outside, for example by means of a controlled lifting device.

BRIEF DESCRIPTION OF THE DRAWINGS

The following description of preferred embodiments of the invention serves to provide a more detailed explanation, in conjunction with the drawings, in which:

FIG. 2: is a perspective view of the closing flap of the container of FIG. 1 prior to insertion of the locking member;

FIG. 3: is a sectional view along line 3—3 of FIG. 1 with the closing flap in the closed position (continuous lines) and in the open position (dash-dotted lines) and FIG. 4: is a view along line 4—4 of FIG. 1 with the closing flap in the closed position (continuous lines) and in the open position (dash-dotted lines).

DETAILED DESCRIPTION OF THE INVENTION

Figure 1:
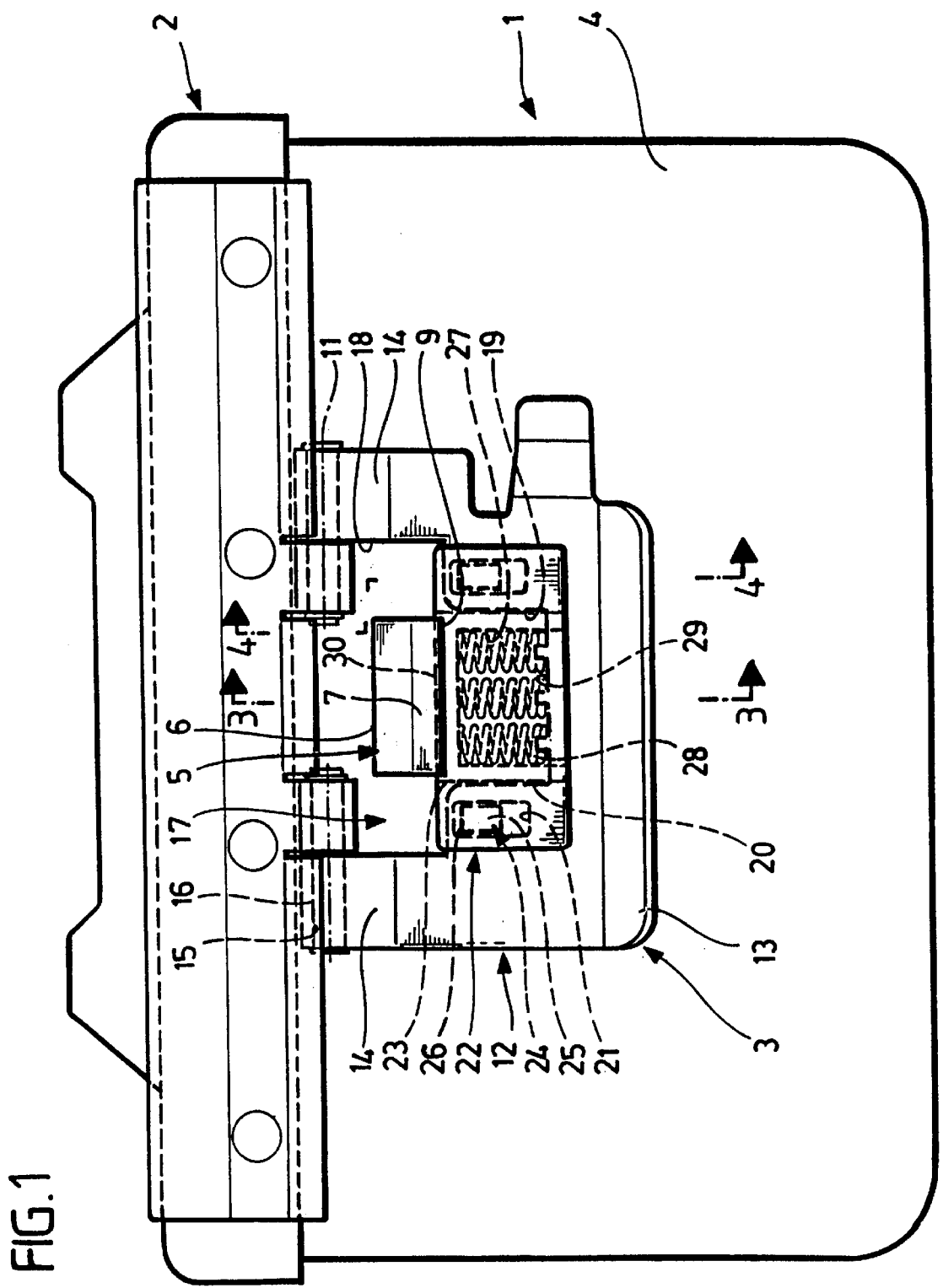
FIG. 1: is a side view of a closed sterile container with a closing flap with resiliently displaceable locking member.

The sterile container shown in the drawings is substantially cuboid in shape and comprises a tub-shaped lower portion 1 and a similarly tub-shaped lid 2 positioned thereon. Between lower portion 1 and lid 2 there is arranged a surrounding annular seal, not shown in the drawing, which seals the inside of the container in relation to the outside when the lid 2 is clamped against the lower portion 1.

Closures 3 of similar construction are arranged on mutually opposing side walls of the lower portion 1, only one of said closures 3 being described in detail below. The closure 3 comprises a locking lug 5 fixed to the side wall 4 of the lower portion 1 and made, in the exemplary embodiment illustrated, from a thin, bent, resilient metal strip. This locking lug comprises an upper side 6 projecting substantially perpendicularly from the side wall 4 and developing, at the free end of the locking lug 5 remote from the side wall 4, in curved manner into a sliding surface 7 extending obliquely downwards, which is adjoined by an inwardly curved portion 8. In the transitional area between the sliding surface 7 and the portion 8, the locking lug 5 forms a downwardly directed locking projection 9, adjoined by a recess 10 formed by the portion 8.

Through the use of resilient metallic material, the entire locking lug 5 may be capable of slight resilient deformation, such that the locking projection 9 may be displaced upwards in slightly resilient manner.

At the lower edge of the lid 2, a plate-shaped flap 12 is mounted so as to swivel about a swivel axis 11 extending in parallel with the lid edge, the opposite edge portion 13 of side flap 12 from the swivel axis 11 being bent away from the side wall 4, such that it is easier to grip the flap 12 at its free end.

The flap 12 is of substantially U-shaped construction, wherein the two lateral edge portions form arms 14, which are bent round at their free ends to form bearing eyelets 15, said bearing eyelets 15 accommodating a bearing shaft 16 defining the swivel axis 11. This bearing shaft 16 is in turn mounted on the lid 2 by suitable bearing eyelets.

Between the two arms 14, the flap 12 comprises a cutout 17 having a wider area 18 adjoining the swivel axis 11 and a narrower area 19 further from the swivel axis 11. Elongate holes 21 extend along the flap in parallel with the side edge 20 of the narrower area 19.

A substantially cuboid locking member 22 is inserted into the cutout 17, said locking member 22 exhibiting a width which matches the wider area 18 and comprising longitudinal channels 23 which extend from top to bottom at the side walls thereof, into which channels 23 the material of the flap 12 penetrates if the locking member 22 is introduced into the cutout 17 from the open side thereof. Together with the longitudinal channels 23, the flap material thus forms a longitudinal guide from the locking member 22 mounted displaceably in the cutout 17.

Catches 24 projecting into each longitudinal channel 23 are formed on the locking member 22 in the area of the longitudinal channels 23, each of said catches 24 comprising an oblique sliding surface 25 on its underside and a stop surface 26 on its upper side extending perpendicularly to the direction of displacement of the locking member 22. These catches 24 may be pushed resiliently out of the longitudinal channel 23, this being possible due to the inherent resilience of the locking member material 22. They are aligned with the longitudinal channels 23 in the flap, such that, when the locking member 22 is introduced into the output 17, the catches 24 are initially lifted resiliently out of the longitudinal channels 23 when the flap comes to rest on the sliding surface 25 but spring back resiliently after insertion of the locking member and then engage in the elongate holes 21. In this way, the locking member 22 is held captive in the flap, since, when the locking member moves towards the open end of the cutout 17, the stop faces 26 of the catches 24 strike against the ends of the elongate holes 21 and prevent further movement of the locking member.

In the locking member 22, in the area between the elongate holes 21, there is arranged a cuboid receiving chamber 27 open at the bottom, into which, in the exemplary embodiment shown, three helical springs 28 are introduced next to one another. These rest on the one hand on the locking member 22 and on the other hand on the lower edge 29 of the cutout 17 and thus displace the locking member 22 towards the open end of the cutout 17. The helical springs 28 are preferably pretensioned when the locking member 22 is introduced into the cutout 17.

The receiving chamber 27 is large enough for several such helical springs 28 to be arranged next to one another therein, but the user may vary the number of helical springs actually inserted therein in accordance with the desired spring characteristics, that is to say it is perfectly possible even to insert only a single helical spring into the receiving chamber.

Assembly of the flap is thus extremely simple, it being sufficient to insert the desired number of helical springs 28 wit the desired spring characteristics into the locking member and then to introduce the locking member into the cutout 17 until the catches 24 engage in the elongate holes 21, after which the flap may be secured in the same way to the lid, as was the case with conventional flaps.

The top 30 of the locking member 22 takes the form of a locking projection and is rounded. Its position when the helical springs 28 are relaxed is such that, when the flap 12 is swivelled into the closed position, the top 30 comes to rest against the sliding surface 7 of the locking lug 5. In this way, when the flap 12 is closed further, the locking member 22 is inserted into the cutout 17 against the action of the helical spring 28, such that the top 30 of the locking member 22 may pass the locking projection 9. As soon as this has happened, the helical spring 28 forces the top 30 of the locking member 22 into the recess 10 in the locking lug 5, such that the flap 12 is then fixed in the closed position. In this position, the helical spring 28 (or optionally the helical springs 28) clamp(s) the lid 2 against the lower portion 1, the clamping force depending on the characteristics of the helical springs 28 and the number thereof.

To open the container, a degree of force has to be overcome in order to move the locking member 22 over the locking projection 9 through compression of the helical springs 28, such that security is thereby provided against unintentional opening of the container.

The excursion of the helical springs 28 may be relatively long, such that it is also possible to lift the lid slightly away from the lower portion against the force of the helical springs 28. This may be of significance when excess pressure builds up in the container, the above-described resilient design of the locking member 22 then resulting in a safety valve effect allowing excess pressure to be released.

What is claimed is:

1. A sterile container for medical purposes having a tub-shaped lower portion and a lid positionable thereon in sealing manner, which lid may be clamped against the lower portion by a closure, wherein the closure comprises a flap swivellable between an open position and a closed position, said flap having a locking projection, and a locking lug with a recess for accommodating the locking projection when the flap is in the closed position, wherein the locking projection takes the form of a locking member separate from the flap, which locking member is mounted in the flap so as to be resiliently displaceable in a guide in a direction in which it is moved out of the recess in the locking lug.

2. A sterile container according to claim 1, wherein the guide is open at one end and closed at the other end.

3. A sterile container according to claim 2, wherein the open end faces the swivel axis of the flap.

4. A sterile container according to claim 1, wherein the guide is formed by the edge strips of a cutout portion of the flap, which strips engage in lateral longitudinal channels in the locking member.

5. A sterile container according to claim 2, wherein the locking member is held captive in the guide by a limit stop which may be moved resiliently out of engagement when the locking member is introduced into the guide.

6. A sterile container according to claim 5, wherein the limit stop takes the form of a resilient catch, which engages in a recess extending in parallel with the guide.

7. A sterile container according to claim 1, wherein spring means are arranged between locking member and flap.

8. A sterile container according to claim 7, wherein the flap and/or the locking member comprises a receiving space for the spring means.

9. A sterile container according to claim 8, wherein the receiving space is so dimensioned that it may accommodate as spring means several compression springs next to one another.

10. A sterile container according to claim 7, wherein the spring means are pretensioned in the relaxed end position.

11. A sterile container according to claim 1, wherein the locking member is mounted so as to be displaceable in the plane of the flap in the direction of the swivel axis thereof.

12. A sterile container according to claim 11, wherein the flap is of U-shaped construction, with two limbs which define the swivel axis at their free ends and with a central cutout which accommodates the locking member.

13. A sterile container according to claim 1, wherein the locking lug is of resilient construction in such a way that, when the flap swivels, it moves slightly to make way for the locking projection on the flap.

14. A sterile container according to claim 1, wherein:
 said closure is an insertable and releasable closure which clamps the lid resiliently against the lower portion when the closure is in place; and
 even when the closure is in place, the lid may be moved far enough away from the tub-shaped lower portion against a resilient closing force of the closure that an opening is formed between the lid and the lower portion.

15. A sterile container according to claim 14, wherein it is closed completely when the lid is positioned sealingly thereon and the inside thereof is connected with the surroundings only by means of an inlet valve.

16. A sterile container according to claim 14, wherein a lifting element is arranged on the lid, by means of which lifting element the lid may be moved away from the tub-shaped lower portion against the action of the resilient closing force of the closure when the latter is in place.

* * * * *